United States Patent
Glumac et al.

(10) Patent No.: US 10,743,812 B1
(45) Date of Patent: Aug. 18, 2020

(54) IMPLANTABLE MIDDLE EAR DIAGNOSTIC TRANSDUCER

(71) Applicant: Envoy Medical Corporation, St. Paul, MN (US)

(72) Inventors: Daniel E. Glumac, Lino Lakes, MN (US); Peter J. Schiller, Coon Rapids, MN (US)

(73) Assignee: Envoy Medical Corporation, St. Paul, MN (US)

( * ) Notice: Subject to any disclaimer, the term of this patent is extended or adjusted under 35 U.S.C. 154(b) by 379 days.

(21) Appl. No.: 14/204,355

(22) Filed: Mar. 11, 2014

Related U.S. Application Data

(60) Provisional application No. 61/783,917, filed on Mar. 14, 2013.

(51) Int. Cl.
*A61B 5/00* (2006.01)
*H04R 25/00* (2006.01)

(52) U.S. Cl.
CPC .......... *A61B 5/4851* (2013.01); *A61B 5/0051* (2013.01); *H04R 25/305* (2013.01); *H04R 25/606* (2013.01)

(58) Field of Classification Search
CPC .... A61B 5/6815; A61B 5/0051; H04R 25/606
See application file for complete search history.

(56) References Cited

U.S. PATENT DOCUMENTS

| | | | | |
|---|---|---|---|---|
| 4,729,366 A | * | 3/1988 | Schaefer | A61F 2/18 600/25 |
| 5,997,466 A | * | 12/1999 | Adams | H04R 25/606 600/25 |
| 6,264,603 B1 | * | 7/2001 | Kennedy | H04R 25/558 600/25 |
| 9,525,949 B1 | * | 12/2016 | Glumac | H04R 25/00 |
| 2002/0038986 A1 | * | 4/2002 | Magnussen | H01L 41/0906 310/317 |

* cited by examiner

*Primary Examiner* — Daniel L Cerioni
*Assistant Examiner* — Yasmeen S Warsi
(74) *Attorney, Agent, or Firm* — Craig Taylor Law Office, PLLC

(57) ABSTRACT

Methods, devices, and systems for measuring vibration of an implanted elongate vibrating body coupled to a bone of the middle ear. One system includes an elongate vibratory body having a first and second piezoelectric body separated by a central vane. The piezoelectric bodies and central vane can be individually electrically coupleable to an implantable electronic device. The electronic device can have a switch, driving circuitry and sensing circuitry within. In normal use, the driving circuitry is coupled through the switch to drive both piezoelectric bodies causing the vibratory body to vibrate. In diagnostic use, one piezoelectric body is driven while the other piezoelectric body is sensed to detect changes in vibration indicative of decoupling or undesirable impedance of the vibratory body.

9 Claims, 6 Drawing Sheets

IMPLANTABLE MIDDLE EAR DIAGNOSTIC TRANSDUCER

RELATED APPLICATIONS

The present application claims priority to U.S. Provisional Patent Application No. 61/783,917 filed Mar. 14, 2013, titled IMPLANTABLE MIDDLE EAR DIAGNOSTIC TRANSDUCER incorporated herein in its entirety.

TECHNICAL FIELD

The present invention is related generally to implantable medical devices. More specifically, the present invention is related to implantable transducers, which can be used in partial middle ear implantable or total middle ear implantable hearing aid systems.

BACKGROUND

In an anatomically normal human hearing apparatus, sound waves, which represent acoustical energy, are directed into an ear canal by the outer ear (pinna) and impinge upon a tympanic membrane (eardrum) interposed at the terminus of the ear canal between the ear canal and the middle ear space. The pressure of the sound waves effect tympanic vibrations in the eardrum, which then become manifested as mechanical energy. The mechanical energy in the form of tympanic vibrations is communicated to the inner ear by a sequence of articulating bones located in the middle ear space, to which are generally referred as the ossicular chain. The ossicular chain must be intact if acoustical energy existing at the eardrum is to be conducted as mechanical energy to the inner ear. The ossicular chain includes three primary components: the malleus, the incus, and the stapes. The malleus includes respective manubrium, neck, and head portions. The manubrium of the malleus attaches to the tympanic membrane at a point known as the umbo. The head of the malleus, which is connected to the manubrium by the neck portion, articulates with one end of the incus, which provides a transmission path for the mechanical energy of induced vibrations from the malleus to the stapes. The stapes includes a capitulum portion connected to a footplate portion by means of support crura and is disposed in and against a membrane-covered opening to the inner ear, referred to as the oval window. The incus articulates the capitulum of the stapes to complete the mechanical transmission path.

Normally, tympanic vibrations are mechanically conducted through the malleus, incus, and stapes, to the oval window and to the inner ear (cochlea). These mechanical vibrations generate fluidic motion (transmitted as hydraulic energy) within the cochlea. Pressures generated in the cochlea by fluidic motion are accommodated by a second membrane-covered opening between the inner and middle ear, referred to as the round window. The cochlea translates the fluidic motion into neural impulses corresponding to sound perception as interpreted by the brain. However, various disorders of the tympanic membrane, ossicular chain and/or inner ear can occur to disrupt or impair normal hearing.

Hearing loss, which may be due to many different causes, is generally of two types, conductive and sensorineural. Of these types, conductive hearing loss occurs when the normal mechanical pathways for sound to reach the hair cells in the cochlea are impeded, for example, damage to the ossicles or the ossicular chain. Conductive hearing loss may often be helped by use of conventional hearing aids, which amplify sound so that acoustic information does reach the cochlea and the hair cells. In other cases, conductive hearing loss can be helped by the use of a middle ear implant, which essentially augments or bypasses the mechanical conduction of the ossicular chain. Some examples of such a middle ear implant can be found in U.S. Pat. Nos. 4,729,366 and 4,850,962 of Schaefer.

In some types of partial middle ear implantable (P-MEI) or total middle ear implantable (T-MEI) hearing aid systems, sounds produce mechanical vibrations within the ear which are converted by an electromechanical input transducer into electrical signals. These electrical signals are in turn amplified and applied to an electromechanical output transducer. The electromechanical output transducer causes an ossicular bone to vibrate in response to the applied amplified electrical signals, thereby improving hearing.

An electromechanical output transducer used for the purpose of causing an ossicular bone to vibrate may be mounted in or near the middle ear. The transducer, also known as a driver, is generally contained in a housing or enclosure, forming an assembly that facilitates the placement of the transducer within or near the middle ear.

In previous designs, the output transducer assembly is coupled to some part of the middle ear and has its output portion typically coupled to the moving part of the ear, e.g. the stapes or another element in the ossicular chain. The output transducer, which may be a piezoelectric, electromagnetic, electrostatic, or another mechanism, is mechanically coupled to the moving portion of the ear to be vibrated.

One method, for measuring the output vibration of the middle ear element to which the output transducer is coupled, is called Laser Doppler Velocimetry (LDV) or Laser Doppler Vibrometry. LDV typically uses a helium-neon laser, or something similar, and can be used to measure the Doppler shift between incident and reflected light from a vibrating surface such as a middle ear element or a middle ear transducer. This Doppler shift measurement can be used to calculate velocity, displacement, or acceleration of a middle ear element or middle ear transducer. LDV equipment can be expensive, and making LDV measurements in the middle ear can be difficult.

An elongate vibratory body, sometimes called a bimorph, can be used to drive a bone in the middle ear. Often the bimorph will have two piezoelectric layers or bodies disposed on either side of a central conducting vane. When the top layer is caused to expand by application of an electric field, and the bottom layer is caused to contract by application of an electric field, the elongate body or bimorph will bend. Long after the implantation procedure, methods such as LDV obviously cannot be used due to the device residing within human tissue. Being able to measure the tip vibration of an elongate vibratory body while implanted would be desirable.

Undesirable changes may occur long after implantation. It is theoretically possible for the vibratory body to be decoupled from the middle ear bone. The growth of scar tissue, tumors, or other growth could impede the movement of the driven middle ear bone and/or the vibrating body. Fluid buildup could also impede the vibrations. For these and other reasons, measuring the vibration of the driven middle ear bone and/or the vibratory body would also be desirable long after the initial surgery.

SUMMARY

The present application provides methods, devices, and systems for measuring vibration of an implanted vibrating elongate body coupled to a bone of the middle ear. One system includes an elongate vibratory body having a first and a second piezoelectric body separated by a central vane. The piezoelectric bodies and central vane can be individually electrically coupleable to an implantable electronic device. The electronic device can have a switch, driving circuitry and sensing circuitry within. In normal use, the driving circuitry is coupled through the switch to drive both piezoelectric bodies causing the vibratory body to vibrate. In diagnostic use, one piezoelectric body is driven while the other piezoelectric body is sensed to detect changes in vibration indicative of decoupling or undesirable impedance of the vibratory body.

One embodiment provides an implantable system for vibrating a bone in the middle ear. The system can include an elongate vibrator body having a first end region for securing to the skull and a second end region for coupling to a middle ear bone. The elongate vibrator body can include a first elongate piezoelectric body and a second elongate piezoelectric body having a central elongate member disposed therebetween. The system can also include a first elongate electrical conductor electrically coupleable through a switch to the first piezoelectric body, a second elongate electrical conductor electrically coupleable through the switch to the second piezoelectric body, and a third elongate electrical conductor electrically coupled to the central elongate member.

The system can include an implantable electronic device electrically coupled to the first, second, and third electrical conductors, where the implantable electrical device has driving circuitry for driving the first and second conductors through the switch so as to vibrate the elongate body and also sensing circuitry for sensing the first electrical conductor through the switch so as to sense vibration of the elongate body. The switch can have a first state in which the first and second electrical conductors are both coupled to the driving circuitry to establish a varying potential over time between the first and second conductors and the third conductor so as to vibrate the elongate body. The switch can also have a second state in which the second electrical conductor is coupled to the driving circuitry to establish a varying potential over time between the second conductor and the third conductor so as to vibrate the elongate body. In this second state the driving circuitry is decoupled from the first electrical conductor, and the sensing circuitry is coupled to the first electrical conductor so as to sense the vibration of the elongate vibrator body.

Systems can also include a switch control for switching the switch between the first and second states. The system can include executable logic for periodically switching the switch between the first and second states. In some systems the sensing circuitry is decoupled from the first electrical conductor in the first state. The first, second, and third conductors can extend between the implantable device and the elongate vibrator body through a cable.

In some systems the switch control is disposed within the implantable device. In some systems the switch control is externally magnetically actuable and may reside within or outside of the implantable electronic device. In various embodiments the switch may exist as a single device or as more than one device.

Some embodiment systems include executable control logic for detecting increased vibrational impedance over time using differences in the sensed vibration over time. The executable control logic may include logic for detecting uncoupling of the elongate vibrational body over time using differences in the sensed vibration over time.

One embodiment method is provided for measuring the vibration of an implanted elongate vibrator body coupled to a bone of a middle ear, where the elongate vibrator body includes at least a first and a second piezoelectric body each disposed on opposite sides of an elongate central member, and where the piezoelectric bodies are individually electrically connectable with respect to each other. This configuration can serve to allow forcing vibration of the elongate vibrator body by electrically driving first and second bodies from an electrical excitation source at a desired frequency. The method can include electrically driving the first piezoelectric body without driving the second piezoelectric body in a pattern to cause vibration of the elongate vibrator body. The method can include measuring electrical potential from the second piezoelectric body during the elongate vibrator body vibration to obtain a first measurement.

Some methods also include comparing the first measurement to a second measurement previously obtained, and using the comparison to determine whether the elongate vibrator body has become decoupled from the middle ear bone. Some such methods include determining whether the elongate vibrator body has become decoupled at least in part by detecting an increased vibrational amplitude from the second measurement to the first measurement. Methods can include determining whether the elongate vibrator body has become decoupled at least in part by detecting a spike in amplitude above a normal roll off frequency, where the spike was added after the second measurement.

Some methods also include comparing the first measurement to a second measurement previously obtained, and using the comparison to determine whether the elongate vibrator body vibration has become additionally impeded since the second measurement was taken. Such methods can include determining whether the elongate vibrator body has become decoupled at least in part by detecting a decreased vibrational amplitude from the second measurement to the first measurement. In some methods the first measurement is taken by an implanted device coupled to the elongate vibrator body. In some methods the first and second measurements are taken by an implanted device coupled to the elongate vibrator body.

DETAILED DESCRIPTION

Figure 1:
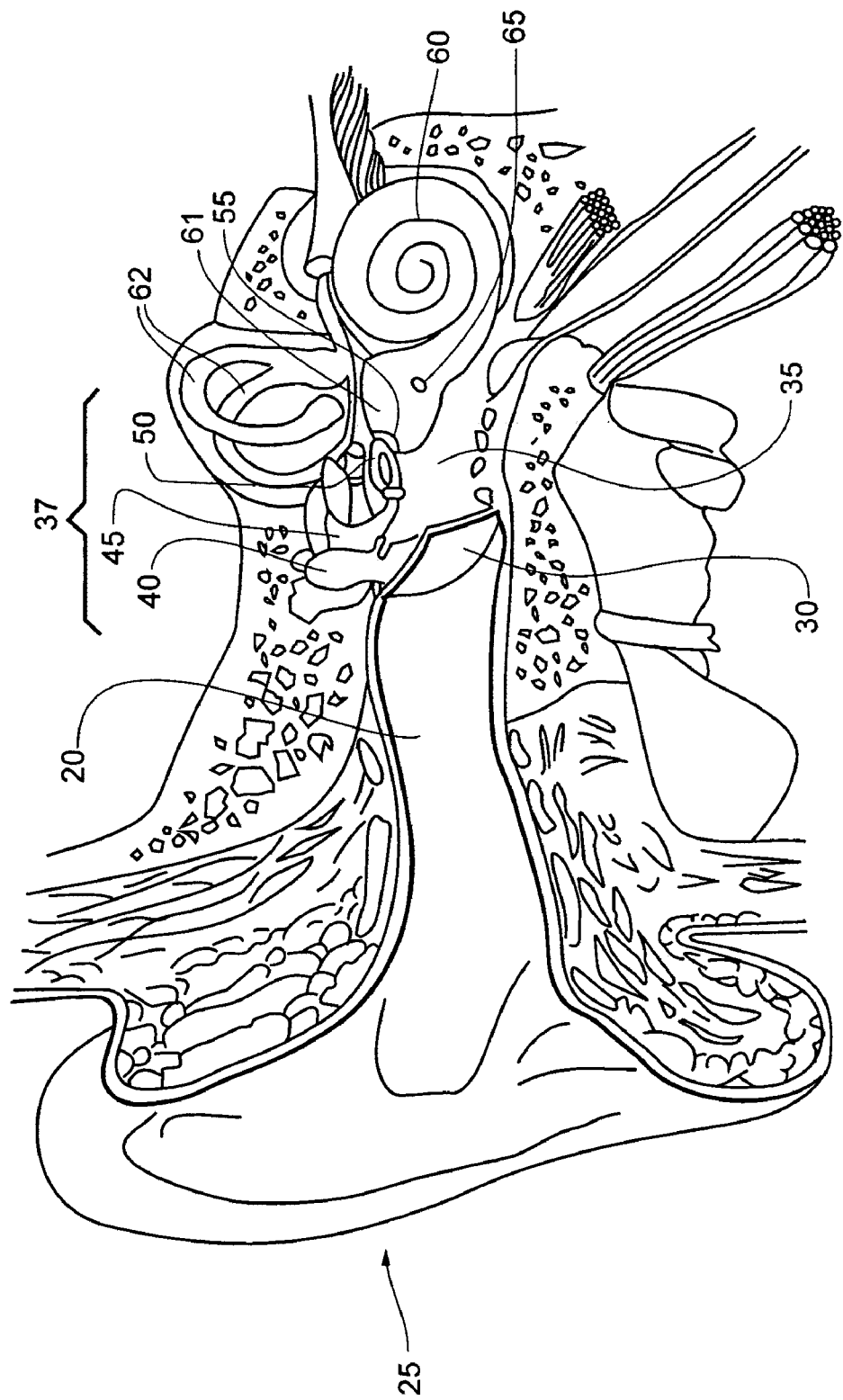
FIG. 1 illustrates a frontal section of an anatomically normal human right ear.

The following detailed description should be read with reference to the drawings, in which like elements in different drawings are numbered identically unless otherwise indicated. The drawings depict selected embodiments and are not intended to limit the scope of the invention. It will be understood that embodiments shown in the drawings and described below are merely for illustrative purposes, and are not intended to limit the scope of the invention as defined in the claims.

Some embodiments of the invention provide an electromechanical transducer which is particularly advantageous when used in a middle ear implantable hearing aid system, such as a partial middle ear implantable (P-MEI), total middle ear implantable (T-MEI), or other hearing aid system. A P-MEI or T-MEI hearing aid system assists the human auditory system in converting acoustic energy contained within sound waves into electrochemical signals delivered to the brain and interpreted as sound.

FIG. 1 illustrates, generally, the human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the ossicular chain transforms acoustic energy at the eardrum to mechanical energy at the cochlea 60.

The ossicular chain 37 includes three primary components: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the hearing aid system according to some embodiments of the invention, tympanic vibrations are mechanically conducted through the malleus 40, incus 45, and stapes 50, to the oval window 55. Vibrations at the oval window 55 are conducted into the fluid filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain 37 lacking sufficient resiliency to transmit mechanical vibrations between the tympanis membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Implantable hearing aid systems have been developed, utilizing various approaches to compensate for hearing disorders. For example, cochlear implant techniques implement an inner ear hearing aid system. Cochlear implants electrically stimulate auditory nerve fibers within the cochlea 60. A typical cochlear implant system may include an external microphone, an external signal processor, and an external transmitter, as well as an implanted receiver and an implanted probe. A signal processor converts speech signals transduced by the microphone into electrical stimulation that is delivered to the cochlea 60.

A particularly interesting class of hearing aid systems includes those which are configured for disposition principally within the middle ear space 35. In middle ear implantable (MEI) hearing aids, an electrical-to-mechanical output transducer couples mechanical vibrations to the ossicular chain 37, which is optionally interrupted to allow coupling of the mechanical vibrations to the ossicular chain 37. Both electromagnetic and piezoelectric output transducers have been used to effect the mechanical vibrations upon the ossicular chain 37.

One example of a partial middle ear implantable (P-MEI) hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus. Such electromagnetic output transducers have relatively high power consumption, which limits their usefulness in total middle ear implantable (T-MEI) hearing aid systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

Piezoelectric output transducers have several advantages over electromagnetic output transducers. The smaller size or volume of the piezoelectric output transducer advantageously eases implantation into the middle ear 35. The lower power consumption of the piezoelectric output transducer is particularly attractive for T-MEI hearing aid systems, which may include a limited longevity implanted battery as a power source.

A piezoelectric output transducer is typically implemented as a ceramic piezoelectric bi-element transducer, which is a cantilevered double plate ceramic element in which two opposing plates are bonded together such that they amplify a piezoelectric action in a direction normal to the bonding plane. Such a bi-element transducer vibrates according to a potential difference applied between the two bonded plates. A proximal end of such a bi-element transducer is typically cantilevered from a transducer mount which is secured to a temporal bone within the middle ear. A distal end of such a bi-element transducer couples mechanical vibrations to an ossicular element such as stapes 50.

Figure 2:
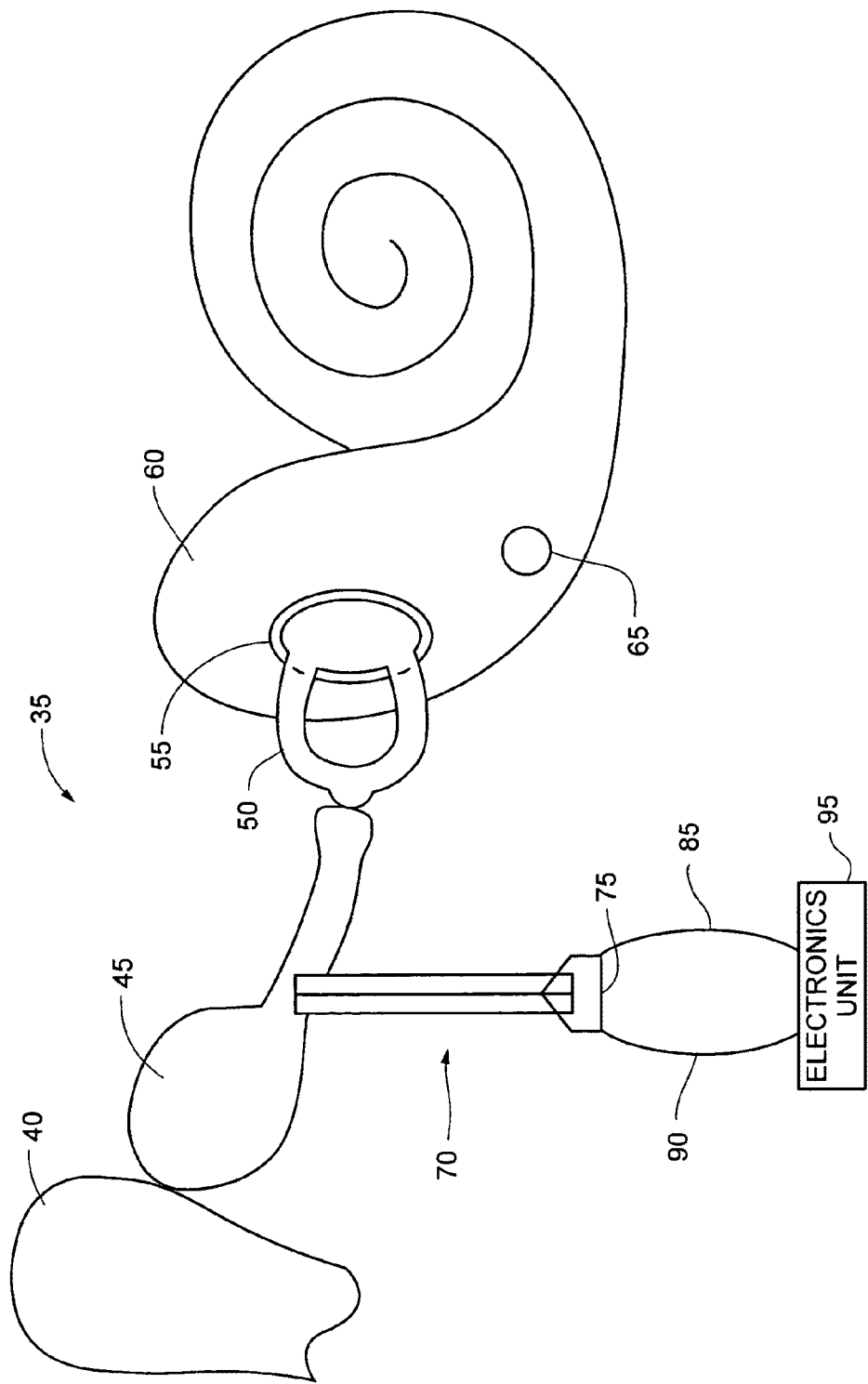
FIG. 2 is a cross-sectional illustration of a typical prior art use of a bi-element transducer coupled to an auditory element in the middle ear.

FIG. 2 is a generalized illustration of a bi-element transducer 70 cantilevered at its proximal end from a mount 75 secured to a temporal bone within middle ear 35. A distal end of bi-element transducer 70 is mechanically coupled to an auditory element to receive or effect mechanical vibrations when operating as an input or output transducer respectively. For example, to receive mechanical vibrations as an input transducer, bi-element transducer 70 may be coupled to an auditory element such as a tympanic membrane 30 (shown in FIG. 1), malleus 40, or incus 45. In another example, to effect vibrations as an output transducer, bi-element transducer 70 may be coupled to an auditory element such as incus 45, stapes 50, oval window 55, round window 65, vestibule 61 (shown in FIG. 1), or semicircular canal 62. The transducer 70 is coupled by leads 85 and 90 to an electronics unit 95.

Figure 3:
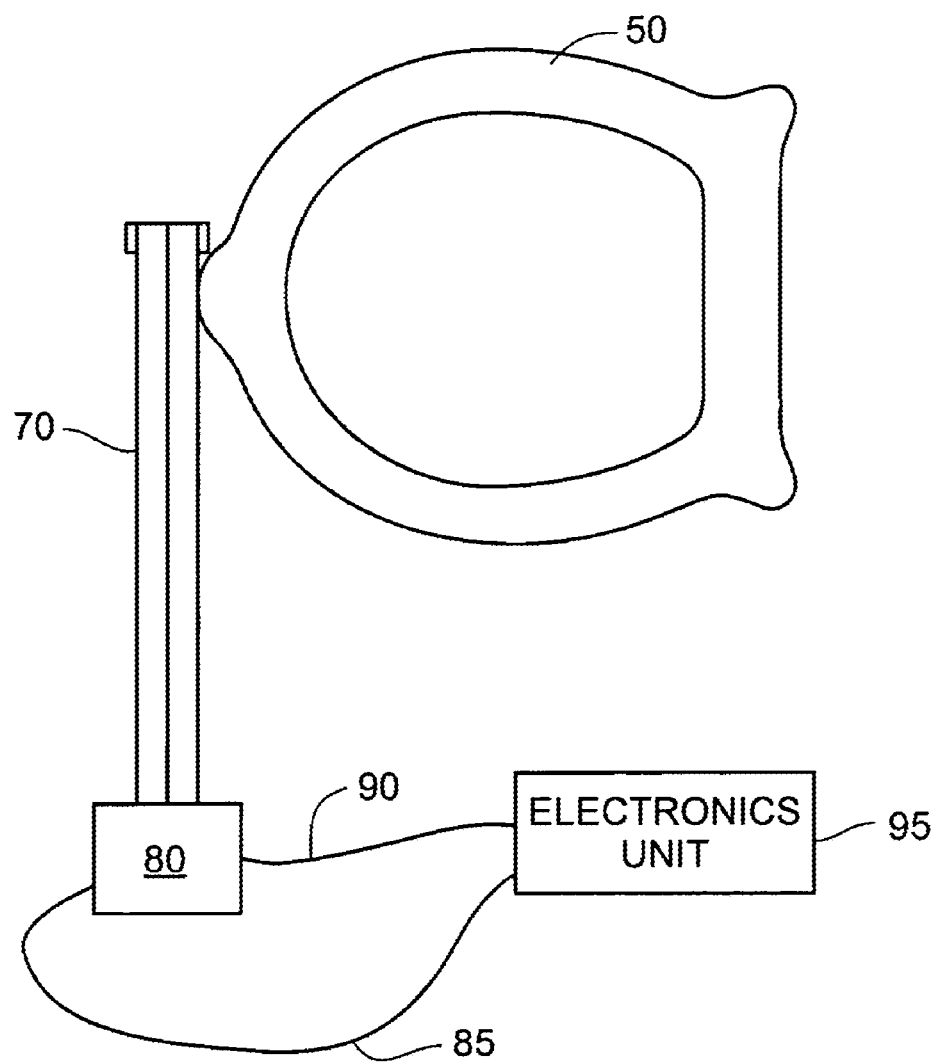
FIG. 3 is a cross-sectional illustration of a prior art bi-element transducer secured only to a vibrated auditory element.

FIG. 3 illustrates generally a cross-sectional view of an electromechanical output transducer. A piezoelectric element, more particularly bi-element transducer 70, is mechanically coupled, and preferably secured, at its proximal end to middle ear 35 (shown in FIG. 1) through an auditory element, preferably stapes 50, or alternatively incus 45, stapes 50, oval window 55, round window 65, vestibule 61, or semicircular canals 62. Bi-element transducer 70 can be secured only to stapes 50 by any known attachment technique, including biocompatible adhesives or mechanical fasteners. For example, in one embodiment, a deformable wire (not shown) secured to the proximal end of bi-element transducer 70 is looped through an inner portion of stapes 50, for example, and crimped to secure bi-element transducer 70 to stapes 50.

Electronics unit 95 may couple an electrical signal through lead wires 85 and 90 to any convenient respective connection points on respective opposing elements of bi-element transducer 70.

In response to the electrical signals received from electronics unit 95, bi-element transducer 70 bends with respect to a longitudinal plane between its opposing elements. The bending is resisted by inertial mass 80 which may be connected to bone through the use of adhesive or bone cement or a mechanical connector, for example a screw, thus mechanically coupling a force to stapes 50 through bi-element transducer 70. This force upon stapes 50 is in turn transmitted to cochlea 60 at oval window 55.

Figure 4:
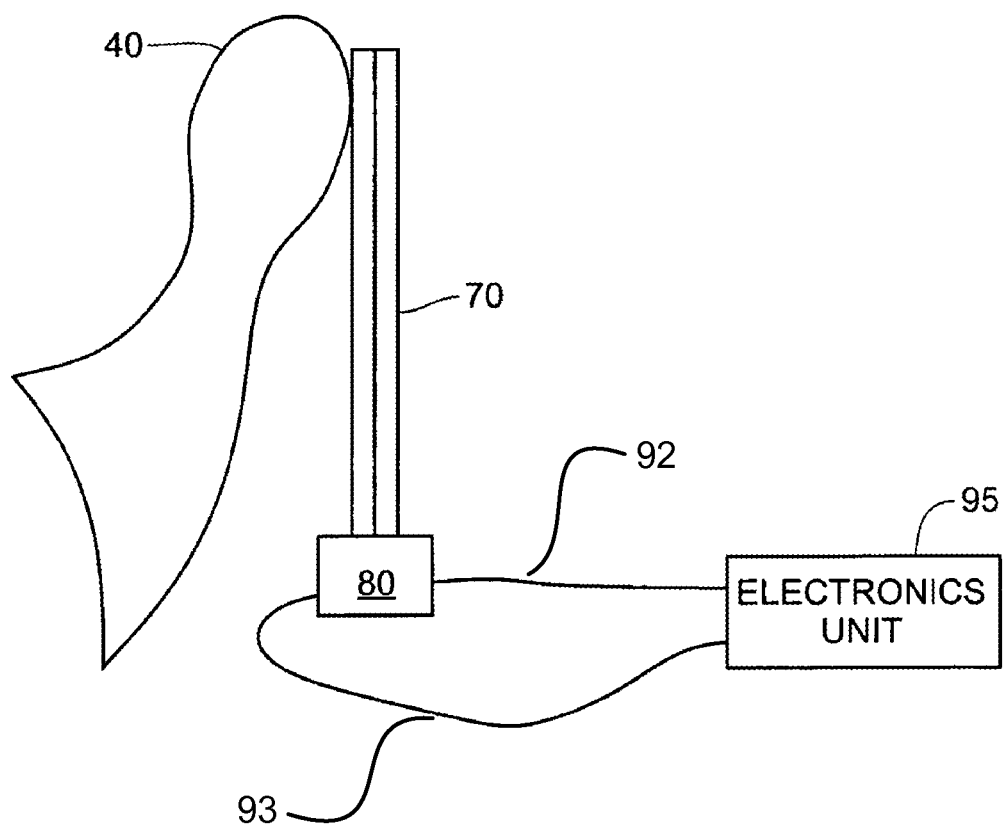
FIG. 4 is a cross-sectional illustration of a prior art bi-element transducer secured only to a vibrating auditory element.

FIG. 4 illustrates generally a cross-sectional view of an electromechanical input transducer. A piezoelectric element, such as bi-element transducer 70, is secured by any known attachment technique at its proximal end, such as described above, for example, to malleus 40.

Bi-element transducer 70 may also be secured only to other auditory elements for receiving mechanical vibrations, such as incus 45 or tympanic membrane 30. Vibrations of malleus 40 cause, at the proximal end of bi-element transducer 70, vibratory displacements that are opposed by inertial mass 80 which may be connected to bone through the use of adhesive or bone cement or a mechanical connector, for example a screw. As a result, bi-element transducer 70 bends with respect to the longitudinal plane between its opposing elements. A resulting electrical signal is provided at any convenient connection point on respective opposing elements of bi-element transducer 70, through respective lead wires 92 and 93 to electronics unit 95.

The ossicular chain can be severed at some part to break the normal sound conduction path from the ear drum (tympanic cavity), through the malleus handle through the malleus lateral process to the malleus head, then to the incus, to the incus lenticular process, to the limbs of the stapes, to the base of the stapes and to the oval (vestibular) window. In practice, the connection between the malleus and incus, or incus and stapes, can be severed, with the vibration sensor attached to the more outer portion of the severed connection and the vibrator/transducer attached to the portion of the severed connection closer to the oval window.

In previous devices, the sensor is a piezoelectric sensor and the vibrator is also a piezoelectric device. The sensor signal carries the sensed vibrations as electrical signals to the implanted medical device which can amplify the signal and the amplified electrical signal carried to the vibrator to drive the stapes or other bone to vibrate the oval window.

The proximal ends and the heads of the sensor and the transducer can both be located within a pocket carved out from the mastoid bone of the skull located behind the ear. In some current methods, both the sensor and the driver are cemented in place after securing the distal ends of the devices to the appropriate bones.

In many embodiments of the present invention, the implanted electronic device is disposed within a pocket formed in the skull by removing a portion of the skull after lifting the flap of skin. A sensor lead may extend through a channel formed along the outside of the skull and continuing to the sensor device head which continues by extending into the middle ear (tympanic) cavity. The sensor can sense the vibrations of the moving middle ear bone and transmit the vibrations as an electrical or optical signal to the implanted medical device. After processing and amplification, the transducer, driver, or vibrator lead can extend through a channel formed in the outside of the skull and be coupled to the head of the vibrator which is coupled to the vibrator body which is in turn coupled to the stapes (for example).

In various embodiments of the present invention, the sensor lead may be replaced by a different sensor lead and the driver or vibrator lead can be replaced by a different leads as well. The sensor and vibrator bodies may also be replaced with different devices. In some embodiments, the sensor and or vibrator bodies may still be secured at the proximal region to the skull, but the exact location of the affixed bodies relative to the coupled bones may not be as critical as is currently the case.

If the vibratory body becomes uncoupled from the middle ear bone, applicant believes the end of the vibrating cantilever would vibrate more freely, and there would be a sharp peak at a frequency above the normal roll off frequency. This abnormal sharp peak can be used to detect the decoupling of the bimorph from the middle ear bone.

In normal use, the vibratory piezoelectric body has a first planar piezoelectric body and a second piezoelectric body having a central conductive vane, with the two piezoelectric bodies forming a sandwich with the conductive vane in between them. The conductive vane is typically a metallic body or electrically conductive material.

When used as a vibrator in normal use, the vibrator is driven "in parallel," with the outer piezoelectric bodies driven at a common voltage which is different from the potential of the central vane. In one example, the outer piezoelectric bodies are driven at a positive potential relative to the central vane which causes the bi-morph to bend in a first direction. The potential can be reversed to drive the bimorph in a second direction. The electrical connections to the outer piezoelectric bodies are often effectively wired in common when driven in parallel.

In one aspect of the invention this wiring is different, in a manner not normally considered useful for the vibratory application. In this aspect, the electrical connections to the outer piezoelectric bodies are independently accessible and switchable between both receiving the same voltage and each receiving a voltage independently or one being driven and the other sensed. In one example, one piezoelectric body is alternately driven by applying alternating polarity voltages applied as between one piezoelectric body and the central metallic vane. The other piezo electric body is switched to sensing mode, being coupled to a sensing circuit in the implantable device. The voltage can be sensed between the piezoelectric body and the potential of the central metallic vane. The sensed voltage will change with the deflection of the bimorph. Using one side of the bimorph to sense while the other side is driven is not optimal for vibrating, as the vibration is weaker than with both sides driven. However, the sensed side can be used as a vibration sensor to determine the degree of vibration and this can be compared with the vibration at the time of the initial implantation. The degree of vibration can be used also to determine whether the vibratory body is effectively coupled to the middle ear bone at the time of the initial surgery. This can be done as the vibratory behavior of the vibratory body will be different if the body is freely vibrating as opposed to being coupled to and driving the middle ear bone.

At a time long after the initial surgical implantation the vibratory behavior of the bimorph can be compared with the initial behavior. One change could be the decoupling of the driven bimorph from the middle ear bone. Another change could be added vibratory impedance or impediment to vibration. This impediment could be scar tissue, fluid, disease, unwanted growths, and the like. In some embodiments, the mode of the driven bimorph is periodically switched between the driven mode and the sensed mode to automatically detect significant changes in vibratory behavior. Significant changes could be signaled to the patient and/or to medical professionals. In some methods, the sensing side can be switched to sense either side, to determine if vibration is impeded in one direction more than the other direction.

In some embodiments, the two piezoelectric bodies are not electrically coupled at the body but only within the implanted pulse generator and switchable between modes within that device. One embodiment includes an implantable bimorph piezoelectric body having at least two piezoelectric bodies disposed on opposite sides of a central conductive body, where the piezoelectric bodies are electrically not in communication with each other at the bimorph and where the piezo electric bodies are polarized for parallel operation.

In still another embodiment, the vibratory body includes at least one additional piezoelectric body coupled to the other bodies and used to sense the vibration of the driven vibratory bodies.

Figure 5:
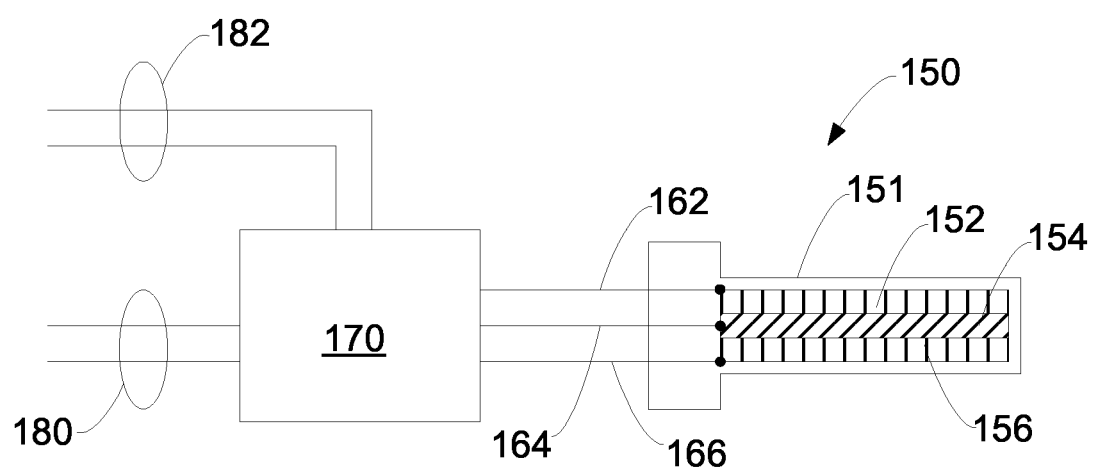
FIG. 5 is a schematic drawing of a system being switchable between using both piezo electric bodies as vibrators and using one for vibration and one for sensing.

FIG. 5 illustrates an embodiment that uses measured potential/charge from one of the piezoelectric bodies as an indication of the actual vibration of the vibratory body. The vibratory body 150 includes a housing 151, a first piezoelectric body 152 electrically coupled to a wire 162, a center vane 154 electrically coupled to a wire 164, and a second piezoelectric body 156 electrically coupled to a wire 166. A pair of vibration driving wires 180 and a pair of vibration sensing wires 182 can both be coupled to a switch or multiplexer 170 via wires 162, 164, and 166.

Figure 6A:
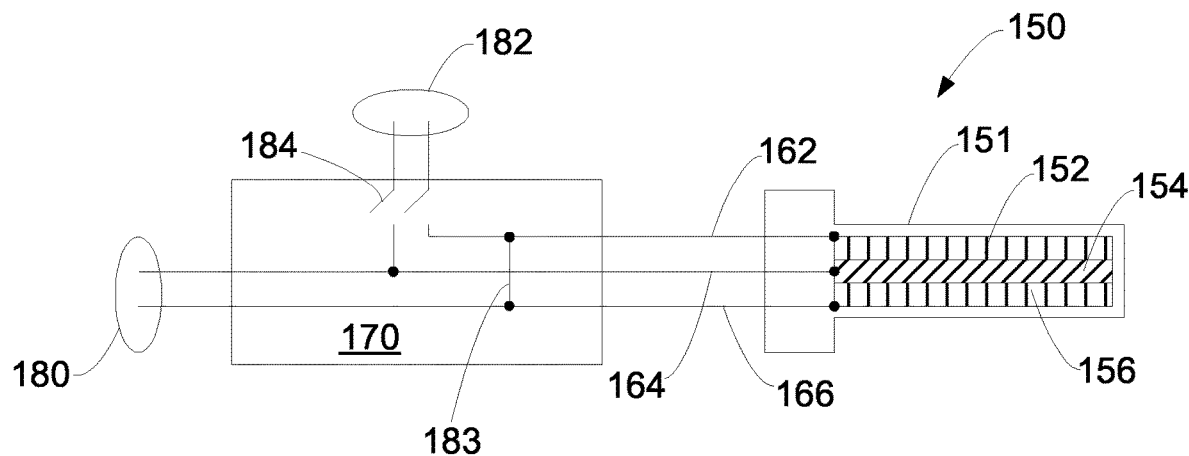
FIG. 6A is a detailed view of the switch of FIG. 7 in a first state.

FIG. 6A shows operation in a normal state in which the piezoelectric bodies 152 and 156 are electrically coupled to each other, as indicated by a closed connection with a switch 183. In normal use, with the piezoelectric bodies 152 and 156 polarized in the same direction, the piezoelectric bodies 152 and 156 are driven electrically in parallel from the input wires 180 and are therefore coupled causing vibratory body 150 to bend. Opposing voltage polarities electrically applied across the piezoelectric layers 152 and 156 cause one layer to contract in the length direction and the other layer to expand in the length direction thereby causing a deflection normal to the length. For example, if a positive voltage value is on the outside of piezoelectric layers 152 and 156 and the center vane 154 is electrical ground, the vibratory body 150 will bend in one direction. If the voltage value is negative, the vibratory body 150 will bend in the opposite direction. When the voltage is varied sinusoidally between positive and negative values, the vibratory body 150 will bend (or vibrate) sinusoidally. The sensor wires 182 may be decoupled with a switch 184 or kept in a high impedance state so as not to interfere with the driven vibrations. In FIG. 6A, switch 170 is in a normal state.

Figure 6B:
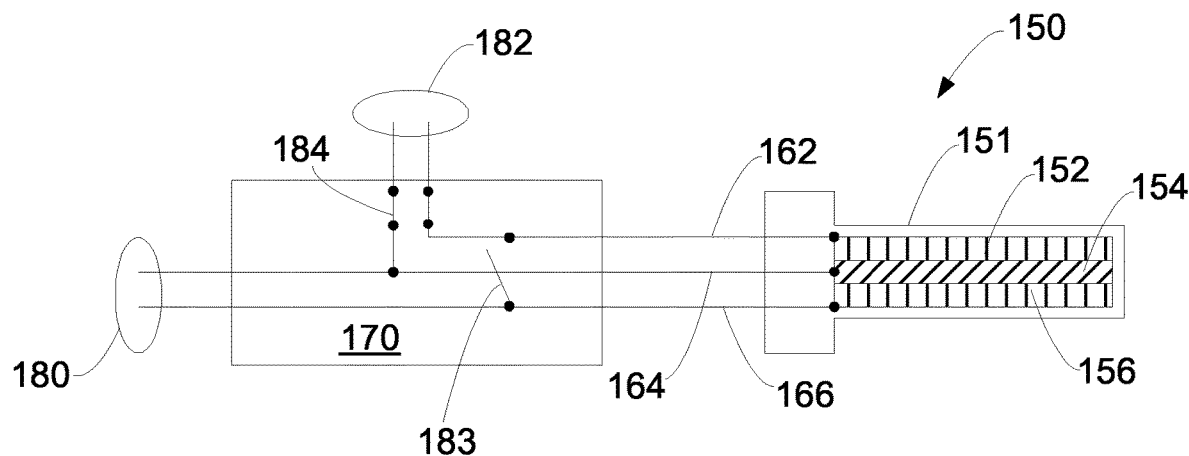
FIG. 6B is a detailed view of the switch of FIG. 7 in a second state.

FIG. 6B shows operation in a diagnostic state in which piezoelectric bodies 152 and 156 are not electrically coupled to each other, as indicated by lack of closed connection of the switch 183. Driving wires 180 are used to drive only one piezoelectric body 152 while the other piezoelectric body 156 is sensed and used as an indication of actual vibration of vibratory body 150. When a voltage is applied to wires 180, and switch 183 is open such that the voltage is applied to the outside piezoelectric body 156 while center vane 154 is at electrical ground, the vibratory body 150 will bend thereby inducing a mechanical stress in piezoelectric body 152 and causing piezoelectric body 152 to output an electric charge that can be measured as a charge or a voltage via wires 182. If the applied voltage is sinusoidal, then the output charge or voltage from piezoelectric body 152 would also be sinusoidal. Sensing wires 182 can be electrically coupled to piezoelectric body wire 162 and center vane wire 164 by closing the switch 184. In FIG. 6B, switch 170 is in a diagnostic state. In this state, the piezoelectric bodies 152 and 156 should not be electrically coupled to each other, including being so coupled in body 150 itself or through housing 151.

In some embodiments, switch 170 can be switched between normal and diagnostic states by executable logic in the implantable electronic device. Executable logic as used herein includes discreet logic, firmware, software, microprocessors, and discrete hardware created with hardware design languages and the like. In some embodiments such a switch is disposed within the implantable electronic device. In other devices such a switch is disposed external to the implantable electronic device. In some embodiments such a switch can be controlled between the normal and diagnostic states using an external electronic signal or a magnetic field, for example using reed switches or Hall Effect devices or the like.

What is claimed is:

1. A method for measuring the vibration of an implanted elongate vibrator body coupled to a bone of a middle ear, where the elongate vibrator body includes at least a first and a second piezoelectric body each disposed on opposite sides of the elongate vibrator body, where the first and second piezoelectric bodies are individually electrically connectable with respect to each other, so as to allow forcing vibration of the elongate vibrator body by electrically driving the first and second piezoelectric bodies from an electrical excitation source at a desired frequency, and allowing measuring vibration from the second piezoelectric body using an electrical sensing circuit, the method comprising:

electrically driving the first piezoelectric body using the electrical excitation source without driving the second piezoelectric body to cause vibration of the elongate vibrator body; and measuring electrical potential from the second piezoelectric body during the elongate vibrator body vibration to obtain a first measurement using the electrical sensing circuit.

2. The method of claim 1 further comprising comparing the first measurement to a second measurement previously obtained prior to the first measurement, and using the comparison to determine whether the elongate vibrator body has become decoupled from the middle ear bone.

3. The method of claim 2 in which determining whether the elongate vibrator body has become decoupled includes detecting an increased vibrational amplitude from the second measurement to the first measurement.

4. The method of claim 2 in which determining whether the elongate vibrator body has become decoupled includes detecting a spike in amplitude above a normal roll off frequency, where the spike was added after the second measurement.

5. The method of claim 1 further comprising comparing the first measurement to a second measurement previously obtained prior to the first measurement, and using the comparison to determine whether the elongate vibrator body vibration has become additionally impeded since the second measurement was taken.

6. The method of claim 5 in which determining whether the elongate vibrator body has become decoupled includes detecting a decreased vibrational amplitude from the second measurement to the first measurement.

7. The method of claim 1 in which the first measurement is taken by an implanted device coupled to the elongate vibrator body.

8. The method of claim 2 in which the first and second measurements are taken by an implanted device coupled to the elongate vibrator body.

9. The method of claim 5 in which the first and second measurements are taken by an implanted device coupled to the elongate vibrator body.

* * * * *